US009744162B1

(12) United States Patent
Habash

(10) Patent No.: US 9,744,162 B1
(45) Date of Patent: Aug. 29, 2017

(54) INCREASING EXPRESSION LEVEL OF APOPTOSIS-RELATED GENES BY TREATING A HUMAN SUBJECT WITH A NITROXIDE

(71) Applicant: Louis Habash, Irvine, CA (US)

(72) Inventor: Louis Habash, Irvine, CA (US)

( * ) Notice: Subject to any disclaimer, the term of this patent is extended or adjusted under 35 U.S.C. 154(b) by 0 days.

(21) Appl. No.: 15/373,250

(22) Filed: Dec. 8, 2016

Related U.S. Application Data

(63) Continuation-in-part of application No. 15/078,911, filed on Mar. 23, 2016, now Pat. No. 9,545,398.

(51) Int. Cl.
*A61K 31/445* (2006.01)

(52) U.S. Cl.
CPC .................. *A61K 31/445* (2013.01)

(58) Field of Classification Search
CPC ................................................ A61K 31/445
See application file for complete search history.

(56) References Cited

PUBLICATIONS

Zou et al. Infection and Immunity, Apr. 2011, vol. 79, No. 4, pp. 1526-1535.*
Gantt et al. The Journal of Immunology, 2001, vol. 167, pp. 893-901.*
Jung et al. Biochemica et Biophysica Acta, 1998, vol. 1425, pp. 387-397.*
Linares et al. Free Radical Biology & Medicine, 2008, vol. 44, pp. 1668-1676.*
Amézaga et al., J. Leukoc. Human scavenger protein AIM increases foam cell formation and CD36-mediated oxLDL uptake, Biol. (2014) 95(3):509-20.
Arai et al., A role for the apoptosis inhibitory factor AIM/Spα/Api6 in atherosclerosis development, Cell Metab. (2005) 1:201-213.
Arakawa et al. The C-Terminal BAG Domain of BAG5 Induces Conformational Changes of the Hsp70 Nucleotide-Binding Domain for ADP-ATP Exchange, Structure (2010) 18(3):309-19.
Arakawa, p53, apoptosis and axon-guidance molecules, Cell Death Differ. (2005) 12(8):1057-65.
Attardi et al., PERP, an apoptosis-associated target of p53, is a novel member of the PMP-22/gas3 family, Genes Dev. (2000) 14(6):704-18.
Bandrés et al., A gene signature of 8 genes could identify the risk of recurrence and progression in Dukes' B colon cancer patients, Oncology Reports (2007) 17(5):1089-1094.
Beaudry et al., Loss of the p53/p63 Regulated Desmosomal Protein Perp Promotes Tumorigenesis, PLoS Genet. (2010) 6(10): e1001168.
Chen et al., PERP gene therapy attenuates lung cancer xenograft via inducing apoptosis and suppressing VEGF, Cancer Biol. Ther. (2011) 12(12):1114-19.
Davies et al., PERP expression stabilizes active p53 via modulation of p53-MDM2 interaction in uveal melanoma cells, Cell Death and Disease (2011) 2:e136.
Davies et al., P53 apoptosis mediator PERP: localization, function and caspase activation in uveal melanoma, J. Cell .Mol. Med. (2009) 13:1995-2007.
Du et al., Decreased PERP Expression on Peripheral Blood Mononuclear Cells from Patient with Rheumatoid Arthritis Negatively Correlates with Disease Activity, Clinical and Developmental Immunology (2013) 2013:256462.
Dusek et al., Deficiency of the p53/p63 target Perp alters mammary gland homeostasis and promotes cancer, Breast Cancer Res. (2012) 14(2):R65.
Flachsbart et al., Investigation of genetic susceptibility factors for human longevity—A targeted nonsynonymous SNP study, Mutat. Res. (2010) 694(1-2):13-19.
Fotinopoulou et al., BRI2 Interacts with Amyloid Precursor Protein (APP) and Regulates Amyloid β (Aβ) Production, J. Biol. Chem. (2005) 280(35):30768-72.
Glass et al. Gene expression changes with age in skin, adipose tissue, blood and brain, Genome Biology 2013, 14:R75.
Gollob et al., Gene Expression Chnages and Signaling Events Associated with the Direct Antimelanoma Effect of IFN-γ, Cancer Res. (2005) 65(19):8869-77.
Gong et al., BRI3 associates with SCG10 and attenuates NGF-induced neurite outgrowth in PC12 cells, BMB Rep. (2008) 41(4):287-93.
Hallstrom et al., PERP, a Host Tetraspanning Membrane Protein, is Required for *Salmonella*-Induced Inflammation, Cell Microbiol. (2015) 17(6):843-59.
Haruta et al., Association of AIM, a Novel Apoptosis Inhibitory Factor, with Hepatitis via Supporting Macrophage Survival and Enhancing Phagocytotic Function of Macrophages, J. Biol. Chem. (2001) 276:22910-22914.
He et al., Akt-phosphorylated PIKE-A inhibits UNC5B-induced apoptosis in cancer cell lines in a p53-dependent manner, Mol. Biol. Cell. (2011) 22(11):1943-54.
Hildebrandt et al., Identification of THW, a putative new tumor suppressor gene, Anticancer Res. (2000) 20(5A):2801-9.
Ihrie et al., Perp Is a p63-Regulated Gene Essential for Epithelial Integrity, Cell (2005) 120(6):843-56.
Ihrie et al., Perp Is a Mediator of p53-Dependent Apoptosis in Diverse Cell Types, Current Biology (2003) 13(22):1985-1990.
Joseph et al. LXR-Dependent Gene Expression is Important for Macrophage Survival and the Innate Immune Response, Cell (2004) 119:299-309.
Kelly et al., Germline Variation in Apoptosis Pathway Genes and Risk of Non-Hodgkin's Lymphoma, Cancer Epidemiol. Biomarkers. Prev. (2010) 19(11):2847-2858.
Kohno et al., Interleukin-17 gene expression in patients with rheumatoid arthritis, Modern Rheumatology (2008) 18(1):15-22.
Kong et al., Loss of the p53/p63 Target PERP is an Early Event in Oral Carcinogenesis and Correlates with Higher Rate of Local Relapse, Oral Surg. Oral Med. Oral Pathol. Oral Radiol. (2013) 115(1):95-103.

(Continued)

*Primary Examiner* — James D Anderson
(74) *Attorney, Agent, or Firm* — Knobbe, Martens, Olson & Bear, LLP

(57) ABSTRACT

Disclosed herein are methods for counteracting age-related decrease in gene expression or treating age-related diseases, for example cancers and autoimmune diseases, caused by decreased expression levels of a gene associated with the apoptosis pathway, using a nitroxide. Further disclosed are methods for treating a human subject in need of an increased expression level of a gene associated with the apoptosis pathway using a nitroxide.

23 Claims, No Drawings

(56) References Cited

PUBLICATIONS

Kong et al., Interactional expression of netrin-1 and its dependence receptor UNC5B in prostate carcinoma, Tumor Biol. (2013) 34(5):2765-72.

Kuwata et al., Role of AIM in *Corynebacterium*-induced granuloma formation in mice, Comp. Hepatol. (2004) 3, Suppl. 1:S44.

Liu et al., PKC α regulates netrin-1/UNC5B-mediated survival pathway in bladder cancer, BMC Cancer. (2014) 14: 93.

Liu et al., Clinical significance of UNC5B expression in bladder cancer, Tumor Biol. (2013) 34(4):2099-108.

Llambi et al., The dependence receptor UNC5H2 mediates apoptosis through DAP-kinase, EMBO J. (2005) 24(6):1192-201.

Lowe et al., p53 is required for radiation-induced apoptosis in mouse thymocytes, Nature (1993) 362(6423):847-849.

Lu et al. Gene regulation and DNA damage in the ageing human brain, Nature (2004) 429:883-891.

Marques et al., Mice Lacking the p53/p63 Target Gene *Perp* are Resistant to Papilloma Development, Cancer Res. (2005) 65:6551-6.

Matsuda et al, BR13 Inhibits Amyloid Precursor Protein Processing in a Mechanistically Distinct Manner from Its Homologue Dementia Gene BR12-, J. Biol. Chem. (2009) 284(23):15815-25.

Matsuda et al., The Familial Dementia BR12 Gene Binds the Alzheimer Gene Amyloid-β Precursor Protein and Inhibits Amyloid-β Production, J. Biol. Chem. (2005) 280(32):28912-16.

Matsuda et al., BR12 Inhibits Amyloid β-Peptide Precursor Protein Processing by Interfering with the Docking of Secretases to the Substrate, J. Neurosci. (2008) 28(35):8668-76.

Miyazaki et al., Increased Susceptibility of Thymocytes to Apoptosis in Mice Lacking AIM, a Novel Murine Macrophage-derived Soluble Factor Belonging to the Scavenger Receptor Cysteine-rich Domain Superfamily, J. Exp. Med. (1999) 189:413-422.

Nguyen et al., Loss of the Desmosomal Protein Perp Enhances the Phenotypic Effects of Pemphigus Vulgaris Autoantibodies, J. Invest. Dermatol. (2009) 129(7):1710-8.

Nowak et al., Perp is required for tissue-specific cell survival during zebrafish development, Cell Death and Differentiation (2005) 12(1):52-64.

Okazaki et al., Clinical significance of UNC5B expression in colorectal cancer, Int. J. Oncol. (2012) 40(1):209-16.

Paraoan et al, Expression of p53-induced apoptosis effector PERP in primary uveal melanomas: Downregulation is associated with aggressive type, Exp. Eye. Res. (2006) 83(4):911-19.

Sanjurjo et al., The Scavenger Protein Apoptosis Inhibitor of Macrophages (AIM) Potentiates the Antimicrobial Response against *Mycobacterium tuberculosis* by Enhancing Autophagy, LoS One. (2013) 8(11):e79670.

Sarrias et al., A Role for Human SPα as a Pattern Recognition Receptor, J. Biol. Chem. (2005) 280:35391-35398.

Thiebault et al., The netrin-1 receptors UNC5H are putative tumor suppressors controlling cell death commitment, Proc. Natl. Acad. Sci. U.S.A. (2003) 100(7):4173-78.

Wang et al., BAG5 Protects against Mitochondrial Oxidative Damage through Regulating PINK1 Degradation, PLoS One. (2014) 9(1):e86276.

Wu et al., *bri3*, a novel gene, participates in tumor necrosis factor-α-induced cell death, Biochem. Biophys. Res. Commun. (2003) 311(2):518-24.

Yamazaki et al., Circulating AIM as an Indicator of Liver Damage and Hepatocellular Carcinoma in Humans, PLoS One. (2014) 9(10):e109123.

Zhan et al., PKCα is involved in the progression of kidney carcinoma through regulating netrin-1/UNC5B signaling pathway, Tumor Biol. (2013) 34(3):1759-66.

Zhang et al., [Down-regulated expression of UNC5b related to hepatocellular carcinoma angiogenesis]. Zhonghua Wai Ke Za Zhi (2009) 47(20):1569-73.

\* cited by examiner

INCREASING EXPRESSION LEVEL OF APOPTOSIS-RELATED GENES BY TREATING A HUMAN SUBJECT WITH A NITROXIDE

BACKGROUND

Field

The present disclosure relates generally to the field of age-related diseases and more particularly to treating human subjects with age-related decrease in gene expression and age-related diseases with a nitroxide.

Description of the Related Art

Apoptosis is a process of programmed cell death that occurs in multicellular organisms. Through apoptosis, cells commit suicide as a way to clear unwanted or damaged cells or to prevent uncontrolled growth. Thus, apoptosis plays an essential role in tissue development and function. Dysregulation in the apoptotic pathway, for example decrease or increase in apoptosis, can lead to a number of diseases and conditions, for example, cancers, autoimmune diseases, inflammatory diseases, and infections.

SUMMARY

Some embodiments disclosed herein provide methods for increasing gene expression. The methods, in some embodiments, include identifying a human subject over the age of 35 and having a decrease expression level of a gene associated with the apoptosis pathway; and administering to the human subject an effective amount of a nitroxide antioxidant resulting in an increased expression level of the gene. In some embodiments, the gene is selected from the group consisting of: Cd51, Perp, Unc5b, Bag5 and Bri3. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for increasing the expression level of a gene in a human subject in need thereof, comprising: identifying a human subject having a decreased expression level of a gene associated with the apoptosis pathway; administering to the human subject an effective amount of a nitroxide antioxidant, whereby the expression level of the gene associated with the apoptosis pathway is increased. In some embodiments, the gene is selected from the group consisting of: Cd51, Perp, Unc5b, Bag5 and Bri3. In some embodiments, the decreased expression level of the gene is age-related. In some embodiments, the human subject is over the age of 35. In some embodiments, the human subject is over the age of 45. In some embodiments, the human subject is over the age of 55. In some embodiments, the human subject is over the age of 65. In some embodiments, the decreased expression level of the gene is disease-related. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the disease is age-related. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for reducing risk of a disease in a human subject in need thereof, comprising: identifying a human subject over the age of 35 having an increased risk of a disease due to a decreased expression level of a gene associated with the apoptosis pathway; administering to the human subject an effective amount of a nitroxide antioxidant, whereby the expression level of the gene associated with the apoptosis pathway is increased. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Cd51, Perp, Unc5b, Bag5 and Bri3. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing a cancer and in need of an increased expression level of a gene associated with the apoptosis pathway; administering to the human subject an effective amount of a nitroxide antioxidant, whereby the expression level of the gene associated with the apoptosis pathway is increased. In some embodiments, the cancer can be selected from the group consisting of bladder cancer, colorectal cancer, hepatocellular carcinoma, prostate carcinoma, and kidney carcinoma. In some embodiments, the gene is selected from the group consisting of: Cd51, Perp, Unc5b, Bag5 and Bri3. In some embodiments, the cancer is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing an autoimmune disease and in need of an increased expression level of a gene associated with the apoptosis pathway; administering to the human subject an effective amount of a nitroxide antioxidant, wherein the expression level of the gene associated with the apoptosis pathway is increased. In some embodiments, the autoimmune disease can be selected from the group consisting of rheumatoid/osteoid arthritis, systemic lupus erythematosus (SLE), inflammatory bowel disease, multiple sclerosis, atherosclerosis, and osteoporosis. In some embodiments, the gene is selected from the group consisting of: Cd51, Perp, Unc5b, Bag5 and Bri3. In some embodiments, the gene is Cd51. In some embodiments, the autoimmune disease is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for a disease associated with a decreased apoptosis in a patient in need thereof, comprising: identifying a human subject having or at risk of developing a disease associated with a decreased expression of a gene associated with the apoptosis pathway; administering to the human subject an effective amount of a nitroxide antioxidant, whereby the expression level of a gene associated with the apoptosis pathway is increased. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Cd51, Perp, Unc5b, Bag5 and Bri3. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual over the age of 35 in need of an increased expression level of a gene associated with the apoptosis pathway; and administering to the individual an effective amount of a nitroxide antioxidant to increase the level of expression of the gene associated with the apoptosis pathway. In some embodiments, the gene is selected from the group consisting of: Cd51, Perp, Unc5b, Bag5 and Bri3. In some embodiments, the human subject is over the age of 45. In some embodiments, the human subject is over the age of 55. In some embodiments, the human subject is over the age of 65. In some embodiments, the human subject has a decrease expression level of the gene. In some embodiments, the individual has or is at risk of developing an age-related condition. In some embodiments, the age-related condition comprises increased senescence in a tissue. In some embodiments, the age-related condition comprises inactivation of the apoptosis pathway in a tissue. In some embodiments, the age-related condition comprises increased molecular heterogeneity. In some embodiments, the age-related condition comprises increased functional impairment in a tissue. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual having a disease-related decreased expression level of a gene associated with the apoptosis pathway; and administering to the individual an effective amount of a nitroxide antioxidant to increase the level of expression of the gene associated with the apoptosis pathway. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is selected from the group consisting of: Cd51, Perp, Unc5b, Bag5 and Bri3. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is increased. In some embodiments, the expression level of the gene in an adipose tissue is increased. In some embodiments, the expression level of the gene in blood is increased. In some embodiments, the expression level of the gene in a neuronal tissue is increased. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with the apoptosis pathway is increased. In some embodiments, the individual has a decreased expression level of the gene. In some embodiments, the gene is selected from the group consisting of: Cd51, Perp, Unc5b, Bag5 and Bri3. In some embodiments, the condition is an age-related condition. In some embodiments, the age-related condition comprises increased senescence in a tissue. In some embodiments, the age-related condition comprises inactivation of the apoptosis pathway in a tissue. In some embodiments, the age-related condition comprises increased molecular heterogeneity. In some embodiments, the age-related condition comprises increased functional impairment in a tissue. In some embodiments, the age-related condition is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the human subject is over the age of 35. In some embodiments, the human subject is over the age of 45. In some embodiments, the human subject is over the age of 55. In some embodiments, the human subject is over the age of 65.

DETAILED DESCRIPTION

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present disclosure, the following terms are defined below.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the term "expression" means the detection of a gene product that is expressed or produced by a nucleic acid molecule by standard molecular biology methods, which gene product refers to e.g. an unspliced RNA, an mRNA, a splice variant mRNA, a polypeptide, a post-translationally modified polypeptide, a splice variant polypeptide etc., and specifically products made using an RNA gene product as a template, e.g. cDNA of the RNA.

As used herein, "differential expression" of a gene means that the expression of the gene is at a higher level ("increased expression") or lower level ("decreased expression") in a human subject suffering from a disease, for example cancers and autoimmune diseases, relative to its expression in a normal or control subject. Differential expression includes both quantitative, as well as qualitative, differences in the temporal or cellular expression pattern in a gene or its expression products among, for example, normal and diseased cells, or among cells which have undergone different disease events or disease stages.

As used herein, "increasing the expression level" of a gene means causing the expression of the gene to increase by treating the human subject with a compound, for example a nitroxide antioxidant, such that the expression level of the gene after treatment is higher than the expression level of the gene before treatment in the human subject.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Human Subject Identification

The present disclosure relates to methods of treating age-related alteration in gene expression. It has been shown that the expression level of a number of genes, such as ones playing important roles in cell growth and apoptosis regulation, is decreased or downregulated in aging human beings (Glass et al. Genome Biology 2013, 14:R75, the content of which is hereby incorporated by reference in its entirety). Gene expression changes also play important roles in aging and serve as biomarkers of physiological decline and disease conditions, such as Alzheimer's disease. Decreased gene expression levels, due to accumulation of DNA damages, were observed in the human brain (Lu et al. Nature 429, 883-891 (24 Jun. 2004), the content of which is hereby incorporated by reference in its entirety).

Therefore, disclosed herein are methods of treating a human subject having an age-related decrease or downregulation in gene expression levels, such as those genes associated with the apoptosis pathway. In some embodiments, the human subject can be identified based on the human subject's age, gene expression level, family history, health conditions, medical history, habits, or a combination thereof.

Regardless of the cause of the downregulation, some common terminology can be used. In some embodiments, the expression level of a gene (such as Cd51, Perp, Unc5b, Bag5 or Bri3) in a human subject is considered to be downregulated if the decrease in the expression level of that gene is statistically significant compared to that of a control or a reference. The control or reference can be, for example, a normal healthy population, a population at large, a collection of individuals of the same age or condition or sex, or the same human subject at a different time (e.g., at an earlier time of life when the human subject does not have the disease or condition that results in the downregulation).

In some embodiments, a normal healthy population or a population at large can be a population having the same or similar gender, age, and/or race, compared to the human subject. In some embodiments, the expression level of the gene in the control or reference can be the mean or median expression level of the gene in control subjects in the control or reference subjects in the reference. The decrease in expression level can be statistically significant if the probability of the observed difference occurring not by chance, the confidence level, is greater than a threshold. The threshold can be, or be about, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values.

In some embodiments, the decrease in expression level can be, or be about, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. In some embodiments, the decrease in expression level can be at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or more.

In some embodiments, the human subject may have an age that is, is about, is over 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years old.

In some embodiments, the human subject is identified based on the human subject's expression profiles of one or more genes associated with the apoptosis pathway. Non-limiting exemplary methods for determining the human subject's expression profiles include: amplification techniques such as PCR and RT-PCR (including quantitative variants), hybridization techniques such as in situ hybridization, microarrays, blots, and others, and high throughput sequencing techniques like Next Generation Sequencing (Illumina, Roche Sequencer, Life Technologies SOLID™), Single Molecule Real Time Sequencing (Pacific Biosciences), True Single Molecule Sequencing (Helicos), or sequencing methods using no light emitting technologies but other physical methods to detect the sequencing reaction or the sequencing product, like Ion Torrent (Life Technologies). Non-limiting exemplary methods for determining the human subject's expression profiles include: binding techniques such as ELISA, immunohistochemistry, microarray and functional techniques such as enzymatic assays.

Genes Associated with the Apoptosis Pathway

In some embodiments, administering to the human subject the effective amount of the nitroxide antioxidant results in an increased expression level of a gene, for example a gene associated with the apoptosis pathway. Therefore, some embodiments disclosed herein provide methods for treating an individual in need thereof, comprising identifying an individual having a disease-related decreased expression level of a gene associated with the apoptosis pathway; and administering to the individual an effective amount of a nitroxide antioxidant to increase the level of expression of the gene associated with the apoptosis pathway. Some embodiments disclosed herein provide methods for treating an individual in need thereof, comprising identifying an individual in need of an increased expression level of a gene associated with the apoptosis pathway; and administering to the individual an effective amount of a nitroxide antioxidant to increase the level of expression of the gene associated with the apoptosis pathway.

Non-limiting examples of diseases associated with altered level of apoptosis include cancer; breast cancer; lung cancer; kidney cancer; cancers of the ovary and uterus; cancer of the central nervous system; cancers of the head and neck; melanoma; lymphomas; leukemia; neurological disorders; Alzheimer's disease; Parkinson's disease; Huntington's disease; amyotrophic lateral sclerosis; stroke; cardiovascular disorders; ischemia; heart failure; infectious diseases; bacterial infections; viral infections; autoimmune diseases; systemic lupus erythematosus; autoimmune lymphoproliferative syndrome; rheumatoid arthritis; and thyroiditis.

Non-limiting exemplary genes involved in the apoptosis pathway include those involved in the extrinsic apoptosis pathway (FAS, FASLG, TNFRSF10A, TNFRSF10B, TNFRSF10C, TNFRSF10D, TNFRSF11B, TNFSF10, TNFRSF1A, TNF, FADD, CFLAR), those in the Caspases family (CASP1, CASP2, CASP3, CASP4, CASP5, CASP6, CASP7, CASP8, CASP9, CASP10, CASP14), those in the IAPB family (NAIP, BIRC2, BIRC3, XIAP, BIRC5, BIRC6, BIRC7), those involved in the mitochondrial/intrinsic apoptosis pathway (Bcl-2 family: BCL2, MCL1, BCL2L1, BCL2L2, BCL2A1, BCL2L10, BAX, BAK1, BOK, BID, BCL2L11, BMF, BAD, BIK, HRK, PMAIP1, BNIP3, BNIP3L, BCL2L14, BBC3, BCL2L12, and BCL2L13; and other proteins: APAF1, CYCS, DIABLO, HTRA2, AIFM1, and ENDOG).

The gene associated with the apoptosis pathway can be Cd51, Perp, Unc5b, Bag5 or Bri3. For example, the treatment can result in increased expression levels of Cd51, Perp, Unc5b, Bag5, Bri3, or any combination thereof. The increased expression levels of Cd51, Perp, Unc5b, Bag5, Bri3, or any combination thereof, can increase the level of apoptosis. The increased level of apoptosis can result in a decrease in or disappearance of signs and symptoms of a disease associated with decreased apoptosis, including the curing of the disease associated with decreased apoptosis. In some embodiments, the increased expression levels of Cd51, Perp, Unc5b, Bag5, Bri3, or any combination thereof, can decrease the level of apoptosis. The decreased level of apoptosis can result in a decrease in or disappearance of signs and symptoms of the disease associated with increased apoptosis, including the curing of the disease associated with increased apoptosis.

Cd51

Cd51 is also known as apoptosis inhibitor of macrophage (AIM), Spa, and apoptosis inhibitor 6. Higher Cd51 levels have been observed in younger people, especially in women (Yamazaki et al., PLoS One. (2014) 9(10):e109123, the content of which is incorporated by reference in its entirety). Thus, estrogen can be involved in the increase in circulating Cd51 levels. Consequently, up-regulation of Cd51 by, for example, a nitroxide antioxidant can prevent and counteract age-related diseases caused by lower Cd51 levels.

Cd51 participates in macrophage homeostasis, including macrophage survival by inhibiting apoptosis. Macrophages play a major role in host innate defense. They can be found in tissues, for example, that function in the filtration of blood or lymph fluids, including liver, spleen, lung, and lymph nodes. Macrophages recognize, internalize, and destroy endogenous and foreign substances that may be harmful. Inflammation is a major mechanism to protect organisms from damage in responding to pathogen infection and tissue injury.

Cd51 is an immune regulator that inhibits immune cell apoptosis at the inflammatory sites and functions as a modulator in immune response. Cd51 has been shown to be involved in pattern recognition of bacteria and in the modulation of monocyte inflammatory responses (Sarrias et al., J. Biol. Chem. (2005) 280:35391-35398, the content of which is incorporated by reference in its entirety). Cd51 has been shown to potentiate the antimicrobial response against *Mycobacterium tuberculosis* by enhancing autophagy (Sanjurjo et al., LoS One. (2013) 8(11):e79670, the content of which is incorporated by reference in its entirety). Cd51 has been shown inhibit apoptosis of T cells and natural killer T (NKT) cells from *Corynebacterium parvum*-induced liver granulomas (Kuwata et al., Comp. Hepatol. (2004) 3, Suppl. 1:S44, the content of which is incorporated by reference in its entirety). Cd51 has been shown to prevent apoptosis of $CD4^+CD8^+$(CD4/CD8) double-positive thymocytes induced by dexamethasone and γ-irradiation awaiting maturation in the thymus (Miyazaki et al., J. Exp. Med. (1999) 189:413-422, the content of which is incorporated by reference in its entirety).

Furthermore, Cd51 has been shown to support the survival and the phagocytic activity of macrophages in liver inflammatory (hepatitis) lesions (Haruta et al., J. Biol. Chem. (2001) 276:22910-22914, the content of which is incorporated by reference in its entirety). Cd51 has been shown to be responsible for the resistance to infection with the intracellular bacteria *Listeria monocytogenes* and macrophage survival and bacterial clearance in *L. monocytogenes* infection (Joseph et al. Cell (2004) 119:299-309, the content of which is incorporated by reference in its entirety). Cd51 has been shown to mediate protection of macrophages from the apoptotic effects of oxidized lipids, including oxidized low density lipoprotein (oxLDL). Cd51 has been shown to facilitate cellular adhesion, promotion of lipid accumulation through enhanced CD36-mediated uptake of oxLDL, and macrophage survival within atherosclerotic lesions (Arai et al., Cell Metab. (2005) 1:201-213; Amézaga et al., J. Leukoc. Biol. (2014) 95(3):509-20, the contents of which are incorporated by reference in their entireties). Consequently, up-regulation of Cd51 inhibits immune cell apoptosis and strengthens innate immune response, for example, at lesion sites. And increasing the expression level of Cd51 can be used to treat a human subject with an age-related disease caused by a decreased expression level of Cd51, a human subject having a decreased expression of Cd51, or any combination thereof.

Perp

Perp is an important mediator of stratified epithelial development, cell adhesion, and apoptosis through desmosomal activities. Perp has been shown to be a p53 transcriptional target pro-apoptotic gene expressed in high levels during apoptosis (Ihrie et al., Current Biology (2003) 13(22):1985-1990; Nowak et al., Cell Death and Differentiation (2005) 12(1):52-64, the contents of which are incorporated by reference in their entireties). Perp has been shown to contribute to radiation-induced apoptosis in $CD4^+$ CD8+ thymocytes which undergo p53-dependent apoptotic response (Ihrie et al., Current Biology (2003) 13(22):1985-1990; Lowe et al., Nature (1993) 362(6423):847-849, the contents of which are incorporated by reference in their entireties). Perp induction has been linked to p53-dependent apoptosis, and Perp has been shown to be an effector of p53-dependent apoptosis (Attardi et al., Genes Dev. (2000) 14(6):704-18, the content of which is incorporated by reference in its entirety). Perp has been observed to lead to an enhanced activity of the second mitochondria-derived activator of caspase (Smac) cascade (Chen et al., Cancer Biol. Ther. (2011) 12(12):1114-9, the content of which is incorporated by reference in its entirety). Smac promotes caspases-9 activation. Caspase-9 is an initiator caspase, and is activated and required during apoptosis. Thus, increasing the expression level of Perp can increase apoptosis in a human subject with an insufficient level of apoptosis, possibly caused by a decreased expression of Perp. Increasing the expression level of Perp can increase the expression level of Perp in a human subject who needs an increased expression level of Perp, for example, a human subject having a disease-related decreased expression level of Perp.

Perp has been shown to be required for Salmonella-induced inflammation (Hallstrom et al., Cell Microbiol. (2015) 17(6):843-59, the content of which is incorporated by reference in its entirety). Perp has been linked to human longevity (Flachsbart et al., Mutat. Res. (2010) 694(1-2): 13-9, the content of which is incorporated by reference in its entirety). Thus, increasing the expression level of Perp can be used to treat a human subject with an age-related disease caused by a decreased expression level of Perp, a human subject having a decreased expression of Perp, or any combination thereof.

Perp is a putative tumor suppressor gene and is down-regulated in metastasizing cells, mammary carcinoma cells, and tumor tissues (Hildebrandt et al., Anticancer Res. (2000) 20(5A):2801-9, the content of which is incorporated by reference in its entirety). Downregulation of Perp has been reported in tumors of the ovary, uterus and breast, and in cutaneous melanoma, pancreas and mammary carcinoma cell lines, compared with the respective normal tissues and non-metastasizing cell lines. Loss of heterozygosity for Perp has been shown in cell lines derived from melanoma, breast, pancreas, cervical, prostate and colon carcinoma. Perp has been shown to be significantly downregulated in aggressive monosomy-3 type primary uveal melanoma (UM) tumors, compared to less aggressive disomy-3 type (Davies et al., J. Cell Mol. Med. (2009) 13:1995-2007; Paraoan et al, Exp. Eye. Res. (2006) 83(4):911-9, the contents of which are incorporated by reference in their entireties). Perp expression has been shown to stabilize active p53, thus p53-regulated apoptosis, via modulation of p53-MDM2 interaction in uveal melanoma cells (Davies et al., Cell Death and Disease (2011) 2:e136, the content of which is incorporated by reference in its entirety).

Deficiency of Perp has been shown to alter mammary gland homeostasis and promote cancer (Dusek et al., Breast Cancer Res. (2012) 14(2):R65, the content of which is incorporated by reference in its entirety). Loss of Perp has been shown to promote tumorigenesis (Beaudry et al., PLoS Genet. (2010) 6(10): e1001168, the content of which is incorporated by reference in its entirety). For example, Perp is a tumor suppressor of skin cancer. The lack of Perp has been shown to impair cell adhesion as a result of aberrant desmosome assembly, thereby diminishing tumor development (Marques et al., Cancer Res. (2005) 65:6551-6, the content of which is incorporated by reference in its entirety).

Squamous cell carcinoma (SCC) is a malignant proliferation of the keratinocyte of the epidermis. Perp has been reported to be downregulated during SCC progression, and Perp deficiency has been reported to promote SCC (Beaudry et al., PLoS Genet. (2010) 6(10): e1001168, the content of which is incorporated by reference in its entirety). The loss of Perp expression has been reported to correlate with the progression of oral cavity SCC with increased local relapse (Kong et al., Oral Surg. Oral Med. Oral Pathol. Oral Radiol. (2013) 115(1):95-103, the content of which is incorporated by reference in its entirety). Thus, increasing the expression level of Perp can be used to treat a human subject with cancer such as SCC or oral cavity SCC.

Perp has been shown to be a target of the p53-related transcription factor, p63, involved in maintaining epithelial integrity by promoting desmosomal cell-cell adhesion (Ihrie et al., Cell (2005) 120(6):843-56, the content of which is incorporated by reference in its entirety). Lack of Perp can result in postnatal lethality accompanied by dramatic blisters throughout their stratified epithelia, including the oral mucosa and skin, possibly because of a reduction in desmosome number and compromised desmosome complex formation. Thus, Perp is a critical component of the desmosome in the skin and other stratified epithelia.

Decreased Perp expression level has been shown in peripheral blood mononuclear cells from human subjects with rheumatoid arthritis, and this decreased expression Perp expression negatively correlates with severity and progression of rheumatoid arthritis (Du et al., Clinical and Developmental Immunology (2013) 2013:256462, the content of which is incorporated by reference in its entirety). And Perp may prohibit rheumatoid arthritis by regulating interleukin (IL)-17, which participates in the inflammatory process and disease activity of rheumatoid arthritis (Kohno et al., Modern Rheumatology (2008) 18(1):15-22, the content of which is incorporated by reference in its entirety). Loss of Perp has been shown to enhance the phenotypic effects of pemphigus vulgaris, an autoimmune bullous disease in which autoantibodies against proteins of the desmosomal adhesion complex perturb desmosomal function, leading to intercellular adhesion defects in the oral mucosa and skin (Nguyen et al., J. Invest. Dermatol. (2009) 129(7): 1710-8, the content of which is incorporated by reference in its entirety). Thus, increasing the expression level of Perp can be used to treat a human subject with an autoimmune disease such as rheumatoid arthritis.

Unc5b

Unc5b is also known as Unc5h2. Down-regulation of Unc5b has been shown to significantly inhibit apoptosis (He et al., Mol. Biol. Cell. (2011) 22(11):1943-54, the content of which is incorporated by reference in its entirety). Thus, increasing the expression level of Unc5b can increase apoptosis in a human subject with an insufficient level of apoptosis, possibly caused by a decreased expression of Unc5b. Increasing the expression level of Unc5b can increase the expression level of Unc5b in a human subject who needs an increased expression level of Unc5b, for example, a human subject having a disease-related decrease in the expression level of Unc5b.

The expression of Unc5b has been shown to be down-regulated in multiple cancers, including colorectal, breast, ovary, uterus, stomach, lung, and kidney cancers (Thiebault et al., Proc. Natl. Acad. Sci. U.S.A. (2003) 100(7):4173-8, the content of which is incorporated by reference in its entirety). Unc5b has been shown to mediate p53-dependent apoptosis through death-associated protein kinase (DAP-kinase) (Llambi et al., EMBO J. (2005) 24(6):1192-201;

Arakawa, Cell Death Differ. (2005) 12(8):1057-65, the contents of which are incorporated by reference in their entireties). Up-regulation of Unc5b has been reported to be associated with the antimelanoma effect of IFN-gamma (Gollob et al., Cancer Res. (2005) 65(19):8869-77, the content of which is incorporated by reference in its entirety).

Decreased Unc5b expression has been observed in bladder cancer cells (Liu et al., BMC Cancer. (2014) 14: 93, the content of which is incorporated by reference in its entirety). Decreased Unc5b expression has been shown in prostate carcinoma cells (Kong et al., Tumour Biol. (2013) 34(5): 2765-72, the content of which is incorporated by reference in its entirety). It has been shown that Unc5b emerged more in bladder cancer cells with lower degrees of malignancy than those with higher degrees of malignancy; Unc5b expression in bladder cancer cells was significantly reduced compared to normal bladder cells, and low Unc5b expression was an independent risk factor for postoperative recurrence in patients with different stages and grades bladder cancer (Liu et al., Tumour Biol. (2013) 34(4):2099-108, the content of which is incorporated by reference in its entirety). Unc5b mRNA has been shown to be down-expressed in bladder cancer tissues. Furthermore, human subjects with lower Unc5b expression in tumors have been shown to have significantly higher recurrence rate after curative surgery and poorer prognosis than those with higher Unc5b expression. Unc5b has been shown to be downregulated in kidney carcinoma (Zhan et al., Tumour Biol. (2013) 34(3):1759-66, the content of which is incorporated by reference in its entirety).

Further, Unc5b mRNA expression has been shown to decrease in some colorectal cancer human subjects, and the human subjects with low-Unc5b-expression tumors showed a significantly higher recurrence rate after curative surgery (Okazaki et al., Int. J. Oncol. (2012) 40(1):209-16, the content of which is incorporated by reference in its entirety). Thus, increasing the expression level of Unc5b can be used to treat a human subject with cancer.

Bag5

Bag5 has been shown to function as the nucleotide exchange factor of Hsp70 for the enhancement of protein refolding (Arakawa et al. Structure (2010) 18(3):309-19, the content of which is incorporated by reference in its entirety). Bag5 has been shown to directly interacted with mutations in PTEN-induced kinase 1 (PINK1), and regulated PINK1 degradation via ubiquitin proteasome system (UPS) (Wang et al., PLoS One. (2014) 9(1):e86276, the content of which is incorporated by reference in its entirety). Loss of the stability of PINK1 may contribute to sporadic Parkinson's disease (PD). Bag5 has been reported to protect mitochondria against MPP+– and rotenone-induced oxidative stress. Thus, increasing the expression level of Bag5 can be used to treat a human subject with an age-related disease caused by a decreased expression level of Bag5, a human subject having a decreased expression of Bag5, or any combination thereof.

Bag5 has been reported to be linked to non-Hodgkin lymphoma (Kelly et al., Cancer Epidemiol. Biomarkers. Prev. (2010) 19(11):2847-2858, the content of which is incorporated by reference in its entirety). Thus, increasing the expression level of Bag5 can be used to treat a human subject with cancer such as non-Hodgkin lymphoma.

Bri3

Overexpression of Bri3 has been reported to induce apoptosis, possibly through lysosome (Wu et al., Biochem. Biophys. Res. Commun. (2003) 311(2):518-24, the content of which is incorporated by reference in its entirety). Increasing the expression level of Bri3 can increase the expression level of Bri3 in a human subject who needs an increased expression level of Bri3, for example, a human subject having a disease-related decrease expression level of Bri3.

Reducing Bri3 expression has been shown to increase beta amyloid (Abeta) secretion (Matsuda et al, J. Biol. Chem. (2009) 284(23):15815-25, the content of which is incorporated by reference in its entirety). Abeta is the main component of the amyloid plaques found in the brains of Alzheimer patients. Bri3 has been shown to interact with amyloid precursor protein (APP) and inhibits APP processing (Matsuda et al., J. Biol. Chem. (2005) 280(32):28912-6; Matsuda et al., J. Neurosci. (2008) 28(35):8668-76; Fotinopoulou et al., J. Biol. Chem. (2005) 280(35):30768-72, the contents of which are incorporated by reference in their entireties).

Bri3 has been shown to exhibit the ability to stabilize the microtubule network and attenuate the microtubule-destabilizing activity of SCG10 (Gong et al., BMB Rep. (2008) 41(4):287-93, the content of which is incorporated by reference in its entirety). Thus, Bri3 is a critical component of the desmosome in the skin and other stratified epithelia.

Bri3 has also been reported to be down-regulated with colorectal cancer progression (Bandrés et al., Oncology Reports (2007) 17(5):1089-1094, the content of which is incorporated by reference in its entirety). Thus, increasing the expression level of Bri3 can be used to treat a human subject with cancer.

Methods for Counteracting Age-Related Decrease in Gene Expression or Treating a Condition Related to Aging Some embodiments disclosed herein provide methods for counteracting age-related decrease in gene expression or treating an age-related disease, comprising identifying a human subject over the age of 35 and having a decreased expression level of one or more genes associated with the apoptosis pathway or an age-related disease; and administering to the human subject an effective amount of a nitroxide antioxidant. In some embodiments, the methods comprise determining the expression level of one or more genes associated with the apoptosis pathway. However, this may not be necessary in some instances, such as where a decreased expression level of one or more genes associated with the apoptosis pathway can be inferred from the human subject's age, family history, health conditions, medical history, habits, or a combination thereof. In some embodiments, the methods disclosed herein may be used to treat a human subject shows no symptoms of an age-related disease, but is at risk of having an age-related disease. Exemplary risk factors for an age-related disease include, but are not limited to, age, family history, health conditions, medical history, habits, or a combination thereof. In some embodiments, risk factors for an age-related disease comprise a decreased expression level of one or more genes associated with the apoptosis pathway.

In some embodiments, administering to the human subject an effective amount of the nitroxide antioxidant results in an increased expression level of a gene, for example a gene associated with the apoptosis pathway. The gene associated with the apoptosis pathway can be Cd51, Perp, Unc5b, Bag5 or Bri3. The treatment of the human subject with the effective amount of the nitroxide antioxidant can result in an increased expression level of the gene. For example, the treatment can result in increased expression levels of Cd51, Perp, Unc5b, Bag5, Bri3, or any combination thereof. The increased expression levels of Cd51, Perp, Unc5b, Bag5, Bri3, or any combination thereof, can increase the level of apoptosis. The increased level of apoptosis can result in a decrease in or disappearance of signs and symptoms of an age-related disease associated with decreased apoptosis, including the curing of the age-related disease. In some embodiments, the increased expression levels of Cd51, Perp, Unc5b, Bag5, Bri3, or any combination thereof, can decrease the level of apoptosis. The decreased level of apoptosis can result in a decrease in or disappearance of signs and symptoms of the age-related disease associated with increased apoptosis, including the curing of the disease associated with age-related disease associated with increased apoptosis.

In some embodiments, the levels of Cd51, Perp, Unc5b, Bag5, Bri3, or any combination thereof in the connective tissue, muscle tissue, nervous tissue, or epithelial tissue may change after the nitroxide antioxidant is administered. Non-limiting examples of the connective tissue include dense connective tissue, loose connective tissue, reticular connective tissue, adipose tissue, cartilage, bone, and extracellular matrix. Non-limiting examples of the muscle tissue includes smooth muscle tissue, cardiac muscle tissue, and skeletal muscle tissue. Non-limiting examples of the nervous tissue include neural tissue of the central nervous system, neural tissue of the peripheral nervous system, the brain, spinal cord, cranial nerves, spinal nerves, and motor neurons. Non-limiting examples of the epithelial tissue include squamous epithelium, cuboidal epithelium, columnar epithelium, glandular epithelium, ciliated epithelium, and skin.

Some embodiments disclosed herein provide methods for treating a disease related to aging in a human subject in need thereof, comprising identifying a human subject over the age of 35 and having an age-related disease and having a decreased expression level of a gene associated with the apoptosis pathway; and administering to the human subject an effective amount of a nitroxide antioxidant. Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with the apoptosis pathway is increased.

Non-limiting examples of age-related diseases include cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension.

Methods for Increasing Expression Level of a Gene

Some embodiments disclosed herein provide methods for increasing the expression level of a gene in a human subject in need thereof, comprising identifying a human subject having a decreased expression level of a gene associated with the apoptosis pathway; and administering to the human subject an effective amount of a nitroxide antioxidant. Some embodiments disclosed herein provide methods for treating a disease associated with a decreased apoptosis in a patient in need thereof, comprising identifying a human subject having a decreased expression level of a gene associated with the apoptosis pathway; and administering to the human subject an effective amount of a nitroxide antioxidant. The decreased expression level may be age-related, or disease related. In some embodiments, the disease may be cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension, or any combination thereof. Some embodiments disclosed herein provide methods for treating an individual in need thereof, comprising identifying a human subject over the age of 35 in need of an increased expression level of a gene associated with the apoptosis pathway; and administering to the human subject an effective amount of a nitroxide antioxidant. In some embodiments, the methods comprise determining the expression level of one or more genes associated with the apoptosis pathway. However, this may not be necessary in some instances, such as where a decreased expression level of one or more genes associated with the apoptosis pathway can be inferred from the human subject's age, family history, health conditions, medical history, habits, or a combination thereof. In some embodiments, the methods disclosed herein may be used to treat a human subject shows no symptoms of a disease associated with a decreased apoptosis, but is at risk of having a disease associated with a decreased apoptosis. Exemplary risk factors for a disease associated with a decreased apoptosis include, but are not limited to, age, family history, health conditions, medical history, habits, or a combination thereof.

In some embodiments, administering to the human subject an effective amount of the nitroxide antioxidant results in an increased expression level of a gene, for example a gene associated with the apoptosis pathway. The gene associated with the apoptosis pathway can be Cd51, Perp, Unc5b, Bag5 or Bri3. The treatment of the human subject with the effective amount of the nitroxide antioxidant can result in an increased expression level of the gene. For example, the treatment can increase the expression levels of Cd51, Perp, Unc5b, Bag5, Bri3, or any combination thereof. The increased expression of the gene counteracts the decrease in the expression level of the gene.

Methods for Treating Cancer

Some embodiments disclosed herein provide methods for treating cancer in a human subject in need thereof, comprising identifying a human subject having a cancer and in need of an increased expression level of a gene associated with the apoptosis pathway; and administering to the human subject an effective amount of a nitroxide antioxidant. In some embodiments, the methods disclosed herein may be used to treat a human subject shows no symptoms of cancer, but is at risk of having cancer. Exemplary risk factors for cancer include, but are not limited to, age, family history, health conditions, medical history, habits, or a combination thereof. In some embodiments, risk factors for cancer comprise a decreased expression level of one or more genes associated with the apoptosis pathway.

Non-limiting examples of the methods for identifying a human subject having a cancer include colonoscopy; sigmoidoscopy; and high-sensitivity fecal occult blood tests. In some embodiments, methods for identifying a human subject having a cancer include low-dose helical computed tomography; mammography; and pap test and human papillomavirus (HPV) testing. In some embodiments, methods for identifying a human subject having a cancer include alpha-fetoprotein blood test; breast magnetic resonance imaging (MRI); CA-125 test; clinical breast exams and regular breast self-exams; prostate-specific antigen (PSA) testing; skin exams; transvaginal ultrasound; and virtual colonoscopy. In some embodiments, methods for identifying a human subject having a cancer include barium enema; biopsy; bone marrow aspiration and biopsy; bone scan; breast MM for early detection of breast cancer; breast MRI; colonoscopy; computed tomography (CT) scan; digital rectal exam (DRE); blood and platelets testing; bone marrow testing; umbilical cord blood testing; electrocardiogram (EKG) and echocardiogram; endoscopic techniques; fecal occult blood tests; magnetic resonance imaging (MRI); mammography; multi gated acquisition (MUGA) scan; papanicolaou (pap) test; positron emission tomography and computed tomography (PET-CT) scan; sigmoidoscopy; tumor marker tests; ultrasound; upper endoscopy. In some embodiments, methods for identifying a human subject having a cancer include DNA sequencing; detecting presence of single nucleotide polymorphism (SNIP); and detecting the presence of certain protein markers.

In some embodiments, administering to the human subject an effective amount of the nitroxide antioxidant results in an increased expression level of a gene, for example a gene associated with the apoptosis pathway. The gene associated with the apoptosis pathway can be Cd51, Perp, Unc5b, Bag5 or Bri3. The treatment of the human subject with the effective amount of the nitroxide antioxidant can result in an increased expression of the gene. For example, the treatment can result in increased expression levels of Cd51, Perp, Unc5b, Bag5, Bri3, or any combination thereof. The increased expression level of the gene can increase the level of apoptosis. The increased level of apoptosis can result in a decrease in or disappearance of signs and symptoms of the cancer, including the curing of the cancer.

Non-limiting examples of cancer include bladder and other urothelial cancers; breast cancer; cervical cancer; colorectal cancer; endometrial cancer; endometrial cancer; esophageal cancer; liver (hepatocellular) cancer; lung cancer; neuroblastoma cancer; oral cavity and oropharyngeal cancer; ovarian, fallopian tube, and primary peritoneal cancer; prostate cancer; skin cancer; stomach (gastric) cancer; and testicular cancer.

Non-limiting examples of cancer include acute lymphoblastic leukemia, adult; acute myeloid leukemia, adult; adrenocortical carcinoma; aids-related lymphoma; anal cancer; bile duct cancer; bladder cancer; brain tumors, adult; breast cancer; breast cancer and pregnancy; breast cancer, male; carcinoid tumors, gastrointestinal; carcinoma of unknown primary; cervical cancer; chronic lymphocytic leukemia; chronic myelogenous leukemia; chronic myeloproliferative neoplasms; cns lymphoma, primary; colon cancer; endometrial cancer; esophageal cancer; extragonadal germ cell tumors; fallopian tube cancer; gallbladder cancer; gastric cancer; gastrointestinal carcinoid tumors; gastrointestinal stromal tumors; germ cell tumors, extragonadal; germ cell tumors, ovarian; gestational trophoblastic disease; hairy cell leukemia; hepatocellular (liver) cancer, adult primary; histiocytosis, langerhans cell; hodgkin lymphoma, adult; hypopharyngeal cancer; intraocular (eye) melanoma; islet cell tumors, pancreatic neuroendocrine tumors; kaposi sarcoma; kidney (renal cell) cancer; kidney (renal pelvis and ureter, transitional cell) cancer; langerhans cell histiocytosis; laryngeal cancer; leukemia, adult acute lymphoblastic; leukemia, adult acute myeloid; leukemia, chronic lymphocytic; leukemia, chronic myelogenous; leukemia, hairy cell; lip and oral cavity cancer; liver cancer, adult primary; lung cancer, non-small cell; lung cancer, small cell; lymphoma, adult Hodgkin; lymphoma, adult non-hodgkin; lymphoma, aids-related; lymphoma, primary cns; malignant mesothelioma; melanoma; melanoma, intraocular (eye); merkel cell carcinoma; metastatic squamous neck cancer with occult primary; multiple myeloma and other plasma cell neoplasms; mycosis fungoides and the sézary syndrome; myelodysplastic syndromes; myelodysplastic/myeloproliferative neoplasms; myeloproliferative neoplasms, chronic; paranasal sinus and nasal cavity cancer; nasopharyngeal cancer; neck cancer with occult primary, metastatic squamous; non- hodgkin lymphoma, adult; non-small cell lung cancer; oral cavity cancer, lip oropharyngeal cancer; ovarian epithelial cancer; ovarian germ cell tumors; ovarian low malignant potential tumors; pancreatic cancer; pancreatic neuroendocrine tumors (islet cell tumors); pheochromocytoma and paraganglioma; paranasal sinus and nasal cavity cancer; parathyroid cancer; penile cancer; pheochromocytoma and paraganglioma; pituitary tumors; plasma cell neoplasms, multiple myeloma and other; breast cancer and pregnancy; primary peritoneal cancer; prostate cancer; rectal cancer; renal cell cancer; transitional cell renal pelvis and ureter; salivary gland cancer; sarcoma, Kaposi; sarcoma, soft tissue, adult; sarcoma, uterine; mycosis fungoides and the sézary syndrome; skin cancer, melanoma; skin cancer, nonmelanoma; small cell lung cancer; small intestine cancer; stomach (gastric) cancer; testicular cancer; thymoma and thymic carcinoma; thyroid cancer; transitional cell cancer of the renal pelvis and ureter; trophoblastic disease, gestational; carcinoma of unknown primary; urethral cancer; uterine cancer, endometrial; uterine sarcoma; vaginal cancer; and vulvar cancer.

In some embodiments, non-limiting examples of cancer include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyPerproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

Non-limiting examples of the cancer include acute lymphoblastic leukemia, childhood; acute myeloid leukemia/other myeloid malignancies, childhood; adrenocortical carcinoma, childhood; astrocytomas, childhood; atypical teratoid/rhabdoid tumor, childhood central nervous system; basal cell carcinoma, childhood; bladder cancer, childhood; bone, malignant fibrous histiocytoma of and osteosarcoma; brain and spinal cord tumors overview, childhood; brain stem glioma, childhood; (brain tumor), childhood astrocytomas; (brain tumor), childhood central nervous system atypical teratoid/rhabdoid tumor; (brain tumor), childhood central nervous system embryonal tumors; (brain tumor), childhood central nervous system germ cell tumors; (brain tumor), childhood craniopharyngioma; (brain tumor), childhood ependymoma; breast cancer, childhood; bronchial tumors, childhood; carcinoid tumors, childhood; carcinoma of unknown primary, childhood; cardiac (heart) tumors, childhood; central nervous system atypical teratoid/rhabdoid tumor, childhood; central nervous system embryonal tumors, childhood; central nervous system germ cell tumors, childhood; cervical cancer, childhood; chordoma, childhood; colorectal cancer, childhood; craniopharyngioma, childhood; effects, treatment for childhood cancer, late; embryonal tumors, central nervous system, childhood; ependymoma, childhood; esophageal tumors, childhood; esthesioneuroblastoma, childhood; ewing sarcoma; extracranial germ cell tumors, childhood; gastric (stomach) cancer, childhood; gastrointestinal stromal tumors, childhood; germ cell tumors, childhood central nervous system; germ cell tumors, childhood extracranial; glioma, childhood brain stem; head and neck cancer, childhood; heart tumors, childhood; hematopoietic cell transplantation, childhood; histiocytoma of bone, malignant fibrous and osteosarcoma; histiocytosis, langerhans cell; hodgkin lymphoma, childhood; kidney tumors of childhood, wilms tumor and other; langerhans cell histiocytosis; laryngeal cancer, childhood; late effects of treatment for childhood cancer; leukemia, childhood acute lymphoblastic; leukemia, childhood acute myeloid/other childhood myeloid malignancies; liver cancer, childhood; lung cancer, childhood; lymphoma, childhood Hodgkin; lymphoma, childhood non-Hodgkin; malignant fibrous histiocytoma of bone and osteosarcoma; melanoma, childhood; mesothelioma, childhood; midline tract carcinoma, childhood; multiple endocrine neoplasia, childhood; myeloid leukemia, childhood acute/other childhood myeloid malignancies; nasopharyngeal cancer, childhood; neuroblastoma, childhood; non-hodgkin lymphoma, childhood; oral cancer, childhood; osteosarcoma and malignant fibrous histiocytoma of bone; ovarian cancer, childhood; pancreatic cancer, childhood; papillomatosis, childhood; paraganglioma, childhood; pediatric supportive care; pheochromocytoma, childhood; pleuropulmonary blastoma, childhood; retinoblastoma; rhabdomyosarcoma, childhood; salivary gland cancer, childhood; sarcoma, childhood soft tissue; (sarcoma), ewing sarcoma; (sarcoma), osteosarcoma and malignant fibrous histiocytoma of bone; (sarcoma), childhood rhabdomyosarcoma; (sarcoma) childhood vascular tumors; skin cancer, childhood; spinal cord tumors overview, childhood brain and; squamous cell carcinoma (skin cancer), childhood; stomach (gastric) cancer, childhood; supportive care, pediatric; testicular cancer, childhood; thymoma and thymic carcinoma, childhood; thyroid tumors, childhood; transplantation, childhood hematopoietic; childhood carcinoma of unknown primary; unusual cancers of childhood; vaginal cancer, childhood; vascular tumors, childhood; and wilms tumor and other childhood kidney tumors.

Non-limiting examples of cancer include embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

Methods for Treating Autoimmune Diseases

Some embodiments disclosed herein provide methods for treating an autoimmune disease in a human subject in need thereof, comprising identifying a human subject having an autoimmune disease and in need of an increased expression level of a gene associated with the apoptosis pathway; and administering to the human subject an effective amount of a nitroxide antioxidant. In some embodiments, the methods disclosed herein may be used to treat a human subject shows no symptoms of an autoimmune disease, but is at risk of having an autoimmune disease. Exemplary risk factors for an autoimmune disease include, but are not limited to, age, family history, health conditions, medical history, habits, or a combination thereof. In some embodiments, risk factors for an autoimmune disease comprise a decreased expression level of one or more genes associated with the apoptosis pathway.

In some embodiments, administering to the human subject an effective amount of the nitroxide antioxidant results in an increased expression level of a gene, for example a gene associated with the apoptosis pathway. The gene associated with the apoptosis pathway can be Cd51, Perp, Unc5b, Bag5 or Bri3. The treatment of the human subject with the effective amount of the nitroxide antioxidant can result in an increased expression level of the gene. For example, the treatment can result in increased expression levels of Cd51, Perp, Unc5b, Bag5, Bri3, or any combination thereof. The increased expression levels of Cd51, Perp, Unc5b, Bag5, Bri3, or any combination thereof, can increase the level of apoptosis. The increased level of apoptosis can result in a decrease in or disappearance of signs and symptoms of the autoimmune disease, including the curing of the autoimmune disease. In some embodiments, the increased expression levels of Cd51, Perp, Unc5b, Bag5, Bri3, or any combination thereof, can decrease the level of apoptosis. The decreased level of apoptosis can result in a decrease in or disappearance of signs and symptoms of the autoimmune disease, including the curing of the autoimmune disease.

Non-limiting examples of autoimmune diseases include rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, *chlamydia, yersinia* and *salmonella* associated arthropathy, spondyloarthopathy, atheromatous disease/arteriosclerosis, atopic allergy, autoimmune bullous disease, pemphigus vulgaris, pemphigus *foliaceus*, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma). The human antibodies, and antibody portions of the present application can be used to treat humans suffering from autoimmune diseases, in particular those associated with inflammation, including, rheumatoid spondylitis, allergy, autoimmune diabetes, autoimmune uveitis.

Non-limiting examples of autoimmune diseases include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, mycobacterium avium intracellulare, mycobacterium tuberculosis, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, pneumocystis carinii pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjogren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthopathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, viral encephalitis/aseptic meningitis, viral-associated hemaphagocytic syndrome, Wegener's granulomatosis, Wernicke-Korsakoff syndrome, Wilson's disease, xenograft rejection of any organ or tissue, yersinia and salmonella-associated arthropathy and the like.

Nitroxide Antioxidant

Non-limiting examples of the nitroxide antioxidant include 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6-tetramethyl-1-piperidinyloxy (Tempamine), 3-Aminomethyl-PROXYL, 3-Cyano-PROXYL, 3-Carbamoyl-PROXYL, 3-Carboxy-PROXYL, and 4-Oxo-TEMPO. TEMPO can also be substituted, typically in the 4 position, for example, 4-amino, 4-(2-bromoacetamido), 4-(ethoxyfluorophosphonyloxy), 4-hydroxy, 4-(2-iodoacetamido), 4-isothiocyanato, 4-maleimido, 4-(4-nitrobenzoyloxyl), 4-phosphonooxy, and the like.

The use of other nitroxide compounds is also contemplated. According to certain embodiments the nitroxide compound can be selected from the following formulas:

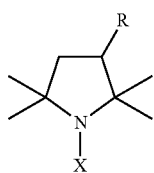

wherein X is selected from O— and OH, and R is selected from COOH, CONH, CN, and $CH_2NH_2$;

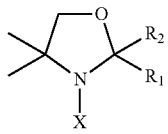

wherein X is selected from O— and OH, and $R_1$ is selected from $CH_3$ and spirocyclohexyl, and $R_2$ is selected from $C_2H_5$ and spirocyclohexyl;

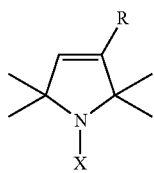

wherein X is selected from O— and OH and R is selected from CONH; and

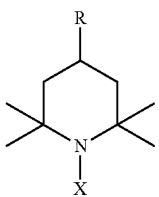

wherein X is selected from O— and OH and R is selected from H, OH, and $NH_2$.

Suitable nitroxide compounds can also be found in Proctor, U.S. Pat. No. 5,352,442, and Mitchell et al., U.S. Pat. No. 5,462,946, both of which are hereby incorporated by reference in their entireties.

Dosage

In some embodiments, the nitroxide antioxidant, non-toxic salts thereof, acid addition salts thereof or hydrates thereof may be administered systemically or locally, usually by oral or parenteral administration. The doses to be administered can be determined depending upon, for example, age, body weight, symptom, the desired therapeutic effect, the route of administration, and the duration of the treatment. In the human adult, the dose per person at a time can be generally from about 0.01 to about 1000 mg, by oral administration, up to several times per day. Specific examples of particular amounts contemplated via oral administration include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 or more mg. The dose per person at a time can be generally from about 0.01 to about 300 mg/kg via parenteral administration (preferably intravenous administration), from one to four or more times per day. Specific examples of particular amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more mg/kg. Continuous intravenous administration can also contemplated for from 1 to 24 hours per day to achieve a target concentration from about 0.01 mg/L to about 100 mg/L. Non-limiting examples of particular amounts contemplated via this route include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more mg/L. The dose to be used does can depend upon various conditions, and there may be cases wherein doses lower than or greater than the ranges specified above are used.

Compositions

The nitroxide antioxidant can be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules. In such solid compositions, Tempol may be admixed with an excipient (e.g. lactose, mannitol, glucose, microcrystalline cellulose, starch), combining agents (hydroxypropyl cellulose, polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or aspartic acid), or the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, the nitroxide antioxidant is dissolved, suspended or emulsified in a commonly used diluent (e.g. purified water, ethanol or mixture thereof). Furthermore, such liquid compositions may also comprise wetting agents or suspending agents, emulsifying agents, sweetening agents, flavoring agents, perfuming agents, preserving agents, buffer agents, or the like.

Injections for parenteral administration include solutions, suspensions, emulsions and solids which are dissolved or suspended. For injections, the nitroxide antioxidant can be dissolved, suspended and emulsified in a solvent. The solvents include, for example, distilled water for injection, physiological salt solution, vegetable oil, propylene glycol, polyethylene glycol, alcohol such as ethanol, or a mixture thereof. Moreover the injections can also include stabilizing agents, agents to assist dissolution (e.g. glutamic acid, aspartic acid or POLYSORBATE80™), suspending agents, emulsifying agents, soothing agents, buffer agents, preserving agents, etc. They can be sterilized in the final process or manufactured and prepared by sterile procedure. They can also be manufactured in the form of sterile solid compositions, such as a freeze-dried composition, and they may be sterilized or dissolved immediately before use in sterile distilled water for injection or some other solvent.

Other compositions for parenteral administration include liquids for external use, and ointment, endermic liniments, inhale, spray, suppositories for rectal administration and pessaries for vaginal administration which comprise the nixtroxide antioxidant and are administered by methods known in the art.

Spray compositions can comprise additional substances other than diluents: e.g. stabilizing agents (e.g. sodium sulfite hydride), isotonic buffers (e.g. sodium chloride, sodium citrate or citric acid). A small aerosol particle size useful for effective distribution of the medicament can be obtained by employing self-propelling compositions containing the drugs in micronized form dispersed in a propellant composition. Effective dispersion of the finely divided drug particles can be accomplished with the use of very small quantities of a suspending agent, present as a coating on the micronized drug particles. Evaporation of the propellant from the aerosol particles after spraying from the aerosol container leaves finely divided drug particles coated with a fine film of the suspending agent. In the micronized form, the average particle size can be less than about 5 microns. The propellant composition may employ, as the suspending agent, a fatty alcohol such as oleyl alcohol. The minimum quantity of suspending agent can be approximately 0.1 to 0.2 percent by weight of the total composition. The amount of suspending agent can be less than about 4 percent by weight of the total composition to maintain an upper particle size limit of less than 10 microns or 5 microns. Propellants that may be employed include hydrofluoroalkane propellants and chlorofluorocarbon propellants. Dry powder inhalation may also be employed.

EXAMPLES

The following examples are offered to illustrate but not to limit the invention.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1. Effects of Tempol on Expression of Genes Associated with the Apoptosis Pathway To assess the effects of Tempol on gene expression, Tempol was administered to experimental mice at a dose of 5 mg/g of food from 14 months to 31 months after birth. Mice receiving the same food without the addition of Tempol were used as a negative control. At the age of 31 months, the experimental animals were sacrificed and the hearts were surgically removed. The expression of a broad spectrum of genes in the cardiac tissue was assessed using chip-based microarray technology. Such chips are well known in the art and are widely used to assess gene expression. The experimental results showed that five genes associated with the apoptosis pathway, Cd51, Perp, Unc5b, Bag5 and Bri3, exhibited statistically significant increase in expression. This result is shown in Table 1.

TABLE 1

Genes Associated With The Apoptosis Pathway Exibiting Increased Expression In Cardiac Tissue After Tempol Administration

| Symbol | Gene title | Control mice | Tempol-treated mice | Fold change | P-value |
|---|---|---|---|---|---|
| Cd51 | CD5 antigen-like | 150 | 406 | 2.70 | 0.01 |
| Perp | TP53 apoptosis effector | 49 | 82 | 1.66 | 0.05 |
| Unc5b | Unc-5 homolog B | 103 | 172 | 1.66 | 0.01 |
| Bag5 | Bcl-2-associated athanogene 5 | 300 | 370 | 1.24 | 0.04 |
| Bri3 | Brain protein I3 | 1549 | 1835 | 1.18 | 0.00 |

Example 2. Treating Age-Related Decrease in Gene Expression

A 70-kilogram human subject over the age of 65 is identified for decreased expression level of Cd51, Perp, Unc5b, Bag5 or Bri3. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 3. Treating a Human Subject with Decreased Gene Expression

A 70-kilogram human subject is identified for decreased expression level of Cd51, Perp, Unc5b, Bag5 or Bri3. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 4. Treating a Human Subject with Age-Related Disease

A 70-kilogram human subject over the age of 65 and having a cardiovascular disease is identified for decreased expression level of Cd51, Perp, Unc5b, Bag5 or Bri3. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 5. Treating a Human Subject at Risk of Developing Cancer

A 70-kilogram human subject at risk of developing colorectal cancer is identified for decreased expression level of Cd51, Perp, Unc5b, Bag5 or Bri3. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 6. Treating a Human Subject at Risk of Developing an Autoimmune Disease

A 70-kilogram human subject at risk of developing rheumatoid arthritis is identified for decreased expression level of Cd51, Perp, Unc5b, Bag5 or Bri3. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

Example 7. Treating a Human Subject at Risk of Developing a Condition Due to Aging A 70-kilogram human subject of 45 years old at risk of developing a condition due to aging is identified. The human subject is administered a dose of 1500 mg of Tempol per day for 180 days. This may be administered in a single dose, or may be administered as a number of smaller doses over a 24-hour period: for example, three 500-mg doses at eight-hour intervals. Following treatment, the serum level of Cd51, Perp, Unc5b, Bag5 or Bri3, is increased.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for treating an individual having an infection, comprising:
    identifying an individual having an infection of a bacterium of the genus *Mycobacterium* or *Corynebacterium*; and
    administering to the individual an effective amount of a nitroxide antioxidant, wherein the nitroxide antioxidant is 4-hydroxy-2,2,6,6-tetramethylpiperidine-1-oxyl,
    whereby the expression level of Cd51 is increased.

2. The method of claim 1, wherein the infection is caused by a bacterium of the genus *Mycobacterium*.

3. The method of claim 2, wherein the bacterium is *Mycobacterium tuberculosis*.

4. The method of claim 1, wherein the infection is a *Mycobacterium avium intracellulare* infection.

5. The method of claim 1, wherein the infection is caused by a bacterium of the genus *Corynebacterium*.

6. The method of claim 5, wherein the bacterium is *Corynebacterium parvum*.

7. The method of claim 1, wherein the individual has a compromised immune system.

8. The method of claim 7, wherein the compromised immune system is age related.

9. The method of claim 8, wherein the individual is over the age of 35.

10. The method of claim 8, wherein the individual is over the age of 55.

11. The method of claim 1, wherein the increased expression level of Cd51 inhibits apoptosis of immune cells.

12. The method of claim 11, wherein the immune cells comprise macrophages or T-cells.

13. The method of claim 1, further comprising inhibiting or delaying development of the infection.

14. A method for treating an individual having an infection, comprising:
    administering to an individual, known to be infected with a bacterium of the genus *Mycobacterium* or *Corynebacterium*, an effective amount of a nitroxide antioxidant, wherein the nitroxide antioxidant is 4-hydroxy-2,2,6,6-tetramethylpiperidine-1-oxyl,
    whereby the expression level of Cd51 is increased.

15. The method of claim 14, wherein the infection is caused by a bacterium of the genus *Mycobacterium*.

16. The method of claim 15, wherein the bacterium is *Mycobacterium tuberculosis*.

17. The method of claim 14, wherein the infection is a *Mycobacterium avium intracellulare* infection.

18. The method of claim 14, wherein the infection is caused by a bacterium of the genus *Corynebacterium*.

19. The method of claim 18, wherein the bacterium is *Corynebacterium parvum*.

20. The method of claim 14, wherein the individual has a compromised immune system.

21. The method of claim 20, wherein the compromised immune system is age related, and wherein the individual is over the age of 35 or 55.

22. The method of claim 14, wherein the increased expression level of Cd51 inhibits apoptosis of immune cells.

23. The method of claim 14, further comprising inhibiting or delaying development of the infection.

* * * * *

UNITED STATES PATENT AND TRADEMARK OFFICE
CERTIFICATE OF CORRECTION

PATENT NO. : 9,744,162 B1  
APPLICATION NO. : 15/373250  
DATED : August 29, 2017  
INVENTOR(S) : Louis Habash Page 1 of 2

It is certified that error appears in the above-identified patent and that said Letters Patent is hereby corrected as shown below:

On the Title Page

In Column 1 (item (56)) at Line 7, Under Publications, change "Biochemica" to --Biochimica--.

In Column 2 (item (56)) at Line 19, Under Publications, change "Chnages" to --Changes--.

In Column 2 (page 2, item (56)) at Line 14, Under Publications, change "LoS" to --PLoS--.

In the Specification

In Column 9 at Line 33, Change "IAPB" to --IAPs--.

In Column 10 at Line 20, Change "LoS" to --PLoS--.

In Column 18 at Line 42, Change "trophobalstic" to --trophoblastic--.

In Column 18 at Line 47, Change "lymphangioendothelio" to --lymphangioendothelioma--.

In Column 18 at Line 51, Change "hyPerproliferative" to --hyperproliferative--.

In Column 20 at Line 18, Change "psteosarcoma," to --osteosarcoma,--.

In Column 21 at Line 4, Change "Schoenlein purpurea," to --Schönlein purpura,--.

In Column 21 at Line 14, Change "greata," to --areata,--.

In Column 21 at Line 15, Change "arthopathy," to --arthropathy,--.

In Column 21 at Line 18, Change "spondyloarthopathy," to --spondyloarthropathy,--.

Signed and Sealed this  
Third Day of July, 2018

Andrei Iancu  
*Director of the United States Patent and Trademark Office*

CERTIFICATE OF CORRECTION (continued)
U.S. Pat. No. 9,744,162 B1

In Column 21 at Line 54, Change "leucopaenia," to --leucopenia,--.

In Column 21 at Line 55, Change "vasulitis" to --vasculitis--.

In Column 22 at Line 3, Change "choleosatatis," to --cholestasis,--.

In Column 22 at Lines 25-26, Change "abetalipoprotemia," to --abetalipoproteinemia,--.

In Column 22 at Lines 57-58, Change "choleosatatis," to --cholestasis,--.

In Column 23 at Line 18, Change "hematophagocytic" to --hemophagocytic--.

In Column 23 at Lines 29-30, Change "Hallerrorden" to --Hallervorden--.

In Column 23 at Line 31, Change "hemachromatosis," to --hemochromatosis,--.

In Column 23 at Line 34, Change "Schoenlein purpurea," to --Schönlein purpura,--.

In Column 23 at Line 41, Change "leucopaenia," to --leucopenia,--.

In Column 23 at Lines 52-53, Change "lymphederma," to --lymphedema,--.

In Column 23 at Line 64, Change "myelodyplastic" to --myelodysplastic--.

In Column 24 at Line 4, Change "epidydimitis," to --epididimitis,--.

In Column 24 at Line 20, Change "supranucleo" to --supranuclear--.

In Column 24 at Line 25, Change "Raynoud's" to --Raynaud's--.

In Column 24 at Line 34, Change "Sjörgren's" to --Sjögren's--.

In Column 24 at Lines 37-38, Change "spondyloarthropathy, spondyloarthopathy," to --spondyloarthropathy,--.

In Column 24 at Line 49, Change "thromboangitis" to --thromboangiitis--.

In Column 24 at Line 61, Change "hemaphagocytic" to --hemophagocytic--.

In Column 27 at Line 47, Change "nixtroxide" to --nitroxide--.

In Column 28 at Line 38 (approx.), Change "Exibiting" to --Exhibiting--.